US010279126B2

(12) United States Patent
Chattaraj et al.

(10) Patent No.: US 10,279,126 B2
(45) Date of Patent: May 7, 2019

(54) FLUID CONDUIT ASSEMBLY WITH GAS TRAPPING FILTER IN THE FLUID FLOW PATH

(71) Applicant: MEDTRONIC MINIMED, INC., Northridge, CA (US)

(72) Inventors: Sarnath Chattaraj, Simi Valley, CA (US); Kiem H. Dang, Thousand Oaks, CA (US); Poonam S. Gulati, La Canada, CA (US); Guangping Zhang, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 801 days.

(21) Appl. No.: 14/508,934

(22) Filed: Oct. 7, 2014

(65) Prior Publication Data
US 2016/0095987 A1  Apr. 7, 2016

(51) Int. Cl.
*A61M 5/38* (2006.01)
*A61M 5/162* (2006.01)
(Continued)

(52) U.S. Cl.
CPC .............. *A61M 5/38* (2013.01); *A61M 5/142* (2013.01); *A61M 5/14244* (2013.01); *A61M 5/162* (2013.01); *A61M 39/10* (2013.01)

(58) Field of Classification Search
CPC .......... A61L 27/14; A61L 27/50; A61L 9/014; A61L 2300/606; A61L 2300/802; A61L 2400/10; A61L 2420/00; A61L 2420/06; A61L 31/10; A61L 31/14; A61M 2005/3131; A61M 2205/70; A61M 39/10; A61M 5/142; A61M 5/14244;
(Continued)

(56) References Cited

U.S. PATENT DOCUMENTS 3,003,500 A  *  10/1961  Barton ................ A61M 5/1424
                                                    210/448
3,631,654 A  *  1/1972  Riely ..................... A61M 5/165
                                                    210/446
(Continued)

FOREIGN PATENT DOCUMENTS

DE        4329229       3/1995
EP        0319268       11/1988
(Continued)

OTHER PUBLICATIONS (Animas Corporation, 1999). Animas . . . bringing new life to insulin therapy.
(Continued)

*Primary Examiner* — Scott J Medway
(74) *Attorney, Agent, or Firm* — Lorenz & Kopf, LLP

(57) ABSTRACT

A fluid delivery system and a fluid conduit assembly suitable for use with the system are disclosed herein. The system includes a fluid infusion pump and a fluid conduit assembly coupled to the pump to deliver medication fluid to a user. The fluid conduit assembly includes a structure defining a flow path for the medication fluid, and a gas trapping filter coupled to the structure and positioned in the flow path. The gas trapping filter functions to filter particulates from the medication fluid and retain gas bubbles from the medication fluid.

10 Claims, 6 Drawing Sheets

(51) Int. Cl.
*A61M 5/142* (2006.01)
*A61M 39/10* (2006.01)

(58) Field of Classification Search
CPC ............ A61M 2205/7527; A61M 5/38; A61M 2205/7536; A61M 5/385; A61M 2005/1657; A61M 5/36; A61M 2005/1403; A61M 2205/12; B01D 19/0031; B01D 46/0012
See application file for complete search history.

(56) References Cited

U.S. PATENT DOCUMENTS

| | | | |
|---|---|---|---|
| 3,631,847 A | 1/1972 | Hobbs, II | |
| 3,650,093 A * | 3/1972 | Rosenberg | A61M 1/0005 604/123 |
| 3,827,562 A * | 8/1974 | Esmond | A61M 1/3627 210/304 |
| 3,882,026 A * | 5/1975 | McPhee | A61M 5/165 210/446 |
| 3,978,857 A * | 9/1976 | McPhee | A61M 5/165 210/446 |
| 4,004,587 A * | 1/1977 | Jess | A61M 5/14 210/314 |
| 4,013,072 A * | 3/1977 | Jess | A61M 5/165 137/177 |
| 4,116,646 A * | 9/1978 | Edwards | A61M 5/165 210/436 |
| 4,190,426 A * | 2/1980 | Ruschke | A61M 5/36 96/6 |
| 4,212,738 A | 7/1980 | Henne | |
| 4,270,532 A | 6/1981 | Franetzki et al. | |
| 4,282,872 A | 8/1981 | Franetzki et al. | |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,459,139 A * | 7/1984 | vonReis | A61M 5/385 210/416.1 |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,571,244 A * | 2/1986 | Knighton | A61M 5/38 210/446 |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,804,360 A * | 2/1989 | Kamen | A61M 5/16809 251/7 |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,183,472 A * | 2/1993 | Jaehrling | A61M 5/14276 128/DIG. 12 |
| 5,195,986 A * | 3/1993 | Kamen | A61M 5/162 128/DIG. 13 |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,308,333 A * | 5/1994 | Skakoon | A61M 5/36 604/110 |
| 5,317,506 A | 5/1994 | Coutre et al. | |
| 5,320,795 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,505,709 A | 4/1996 | Funderburk et al. | |
| 5,497,772 A | 5/1996 | Schulman et al. | |
| 5,522,769 A | 6/1996 | DeGuiseppi | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,490 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,902,281 A * | 5/1999 | Kraus | A61M 5/1411 604/190 |
| 5,904,708 A | 5/1999 | Goedeke | |
| 5,913,310 A | 6/1999 | Brown | |
| 5,917,346 A | 6/1999 | Gord | |

(56) References Cited

U.S. PATENT DOCUMENTS

| | | | |
|---|---|---|---|
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,259,937 B1 | 7/2001 | Schulman et al. | |
| 6,329,161 B1 | 12/2001 | Heller et al. | |
| 6,376,211 B1 * | 4/2002 | Little, II | C12Q 1/18 435/183 |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,621,893 B2 | 11/2009 | Moberg et al. | |
| 9,901,514 B2 * | 2/2018 | Kavazov | A61J 1/2089 |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0077598 A1 | 6/2002 | Yap et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0032945 A1 * | 2/2003 | Jayaraman | A61K 9/009 604/890.1 |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0161042 A1 * | 7/2005 | Fudge | A61B 5/097 128/205.12 |
| 2005/0192557 A1 | 9/2005 | Brauker et al. | |
| 2006/0229530 A1 * | 10/2006 | Hosoda | A61B 5/150022 600/573 |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0105618 A1 * | 5/2008 | Beckius | B01D 63/024 210/650 |
| 2008/0154503 A1 | 6/2008 | Wittenber et al. | |
| 2009/0081951 A1 | 3/2009 | Erdmann et al. | |
| 2009/0082635 A1 | 3/2009 | Baldus et al. | |
| 2013/0303987 A1 * | 11/2013 | Esnouf | A61M 5/36 604/127 |
| 2016/0095987 A1 * | 4/2016 | Chattaraj | A61M 5/38 604/126 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| EP | 2229970 A1 | 9/2010 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |

(56) References Cited

FOREIGN PATENT DOCUMENTS

| WO | WO 98/24358 | 6/1998 |
|---|---|---|
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | PCT/US02/03299 | 10/2002 |
| WO | WO 03/001329 | 1/2003 |
| WO | WO 03/094090 | 11/2003 |
| WO | WO 2005/065538 A2 | 7/2005 |

OTHER PUBLICATIONS

Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1398). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed-Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed-Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no. date).
Disetronic My Choice H-TRONplus Insulin Pump Reference Manual. (no date).
Disetronic H-TRON® plus Reference Manual. (no. date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the Word Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines/MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison/Pump Therapy Will Change Your Life.
(MiniMed, 2000). MiniMed® 508 User's Guide.
(MiniMed Inc., 2000). MiniMed® Now [I] Can Meal Bolus Calculator/MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell" Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp, 43-54.
Gough, D. A., et al., "Two-Dimensional Enzyme Electrode Sensor for Glucose," Analytical Chemistry, vol. 57, No. 5. 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68. No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.

(56) References Cited

OTHER PUBLICATIONS

Kawamori, Ryuzo, et al., "Perfect Normalization of Excessive Glucagon Responses to intraveneous Arginine in Human Diabetes Mellitus With the Artificial Beta-Cell" Diabetes vol. 29, Sep. 1980, pp. 782-765.

Kimuira, J., et al., "An immobilized Enzyme Membrane Fabrication Method," Biosensors 4, 1988, pp. 41-52.

Koudelka, M., et al., "In-vivo Behaviour of Hypodermically Implanted Microfabricated Glucose Sensors," Biosensors & Bioelectronics 6, 1991, pp. 31-36.

Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

Mckean, Brian D., et al., "A Telemetry-Instrumentation System for Chronically Implanted Glucose and Oxygen Sensors," IEEE Transactions on Biomedical Engineering, Vo. 35, No. 7, Jul. 1988. pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artificial endocrine pancreas with the newly designed needle-type glucose sensor," Elsevier Sciences B.V., 1994. pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M. "A Needle-Type Glucose Sensor—A Valuable Tool Not Only for a Self-Blood Glucose Monitoring but for a Wearable Artificial Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4. pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26. pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-342.

Sternberg, Robert, et al., "Study and Development of Multilayer Needle-type Enzyme-based Glucose Microsensors" Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized muiti-enzyme biosensors integrated with pH sensors on flexible polymer carriers for in vivo applciations," Biosensors & Bioelectronics, vol. 7. 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

FLUID CONDUIT ASSEMBLY WITH GAS TRAPPING FILTER IN THE FLUID FLOW PATH

TECHNICAL FIELD

Embodiments of the subject matter described herein relate generally to fluid infusion devices for delivering a medication fluid to the body of a user. More particularly, embodiments of the subject matter relate to the use of a gas trapping filter in the medication fluid flow path.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., continuous insulin infusion devices such as insulin pumps) to deliver controlled amounts of insulin or other drugs to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic), and devices configured for ambulatory or portable use (to be carried by a patient). External fluid infusion devices may establish a fluid flow path from a fluid reservoir to the patient via, for example, a suitable hollow tubing. The hollow tubing may be connected to a hollow fluid delivery needle that is designed to pierce the patient's skin to deliver an infusion fluid to the body. Alternatively, the hollow tubing may be connected directly to the patient's body through a cannula or set of microneedles.

It is desirable to reduce the amount of air bubbles in a medication fluid before delivering the fluid to the patient. Small bubbles may be introduced into the medication fluid during a reservoir filling operation, for example, when the fluid reservoir is filled from a vial using a syringe. Although patients are instructed to eliminate air from a filled reservoir, some micro bubbles may remain.

Accordingly, it is desirable to have an assembly, system, or component that is designed to mitigate the effects of air bubbles within a medication fluid flow path. In addition, it is desirable to have an assembly, system, or component that reduces the presence of air bubbles in a fluid flow path while also filtering particulates and/or unwanted substances from the medication fluid. Furthermore, other desirable features and characteristics will become apparent from the subsequent detailed description and the appended claims, taken in conjunction with the accompanying drawings and the foregoing technical field and background.

BRIEF SUMMARY

Disclosed herein is a fluid conduit assembly for delivery of a medication fluid. An exemplary embodiment of the fluid conduit assembly includes a structure defining a flow path for the medication fluid and a gas trapping filter coupled to the structure. The gas trapping filter is positioned in the flow path to filter particulates from the medication fluid and retain gas bubbles from the medication fluid.

A fluid delivery system is also disclosed herein. An exemplary embodiment of the system includes: a fluid infusion pump to provide a medication fluid; a fluid conduit assembly coupled to the fluid infusion pump; and a gas trapping filter. The fluid conduit delivers the medication fluid to a user, and the fluid conduit assembly defines a flow path for the medication fluid. The gas trapping filter is positioned in the flow path to filter particulates from the medication fluid and retain gas bubbles from the medication fluid.

Also disclosed herein is a fluid conduit assembly for delivery of a medication fluid. An exemplary embodiment of the fluid conduit assembly includes a body section to receive a fluid reservoir, and a flow path defined in the body section. The flow path carries fluid from the fluid reservoir when the body section is coupled to the fluid reservoir. The fluid conduit assembly also has a length of tubing extending from the body section and in fluid communication with the flow path. The length of tubing carries fluid from the body section during a fluid delivery operation. The fluid conduit assembly also has a partially or predominantly hydrophilic gas trapping filter positioned in the flow path to filter particulates from the medication fluid and retain gas bubbles from the medication fluid.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter described here relates to certain assemblies, components, and features of a fluid infusion system of the type used to treat a medical condition of a patient. The fluid infusion system is used for infusing a medication fluid into the body of a user. The non-limiting examples described below relate to a medical device used to treat diabetes (more specifically, an insulin pump), although embodiments of the disclosed subject matter are not so limited. Accordingly, the medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. Moreover, the gas trapping filter described below could be utilized in the context of other fluid delivery systems if so desired.

For the sake of brevity, conventional features and technologies related to infusion system operation, insulin pump and/or infusion set operation, and other functional aspects of the fluid infusion system (and the individual operating components of the system) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

Figure 1:
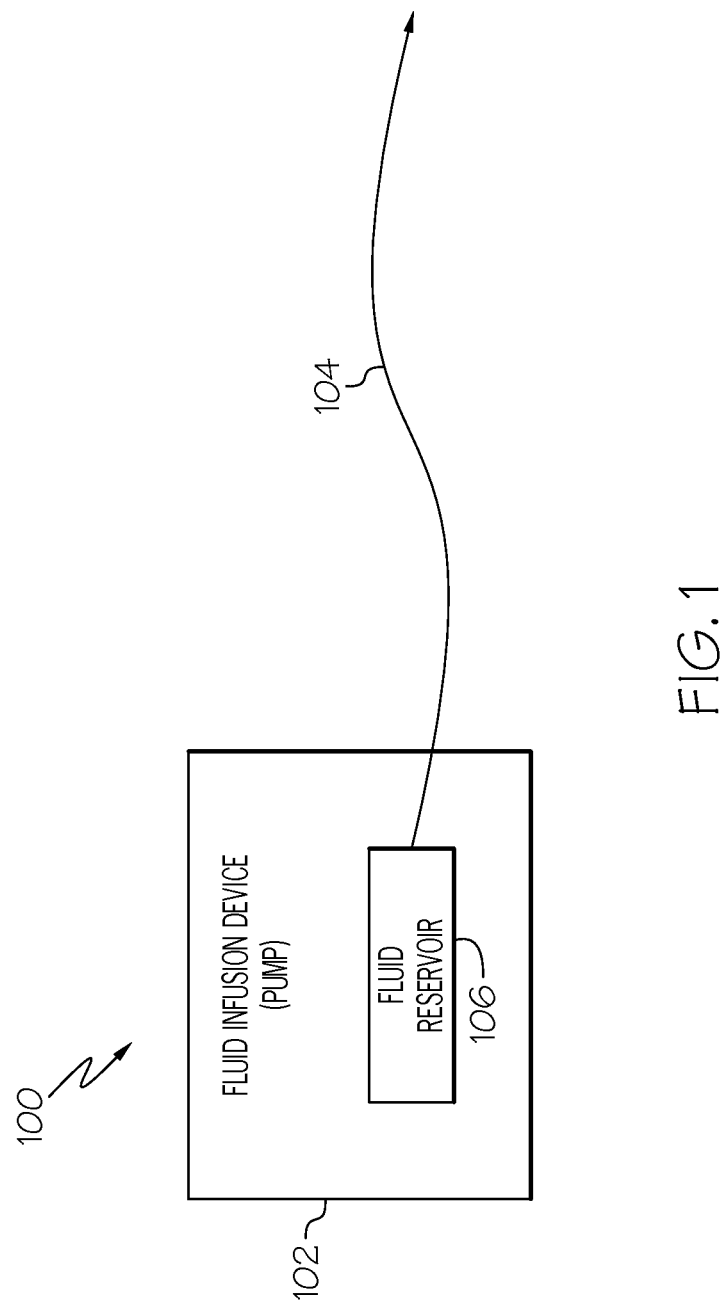
FIG. 1 is a simplified block diagram representation of an embodiment of a fluid delivery system.

FIG. 1 is a simplified block diagram representation of an embodiment of a fluid delivery system 100, which can be utilized to administer a medication fluid such as insulin to a patient. The fluid delivery system 100 includes a fluid infusion device 102 (e.g., an infusion pump) and a fluid conduit assembly 104 that is coupled to, integrated with, or otherwise associated with the fluid infusion device 102. The fluid infusion device 102 includes a fluid reservoir 106 or an equivalent supply of the medication fluid to be administered. The fluid infusion device 102 is operated in a controlled manner to deliver the medication fluid to the user via the fluid conduit assembly 104. Although not depicted in FIG. 1, the fluid delivery system 100 also includes a gas trapping filter that is positioned in the fluid flow path. In certain embodiments, the gas trapping filter is located within the fluid flow path defined by the fluid conduit assembly 104.

Figure 2:
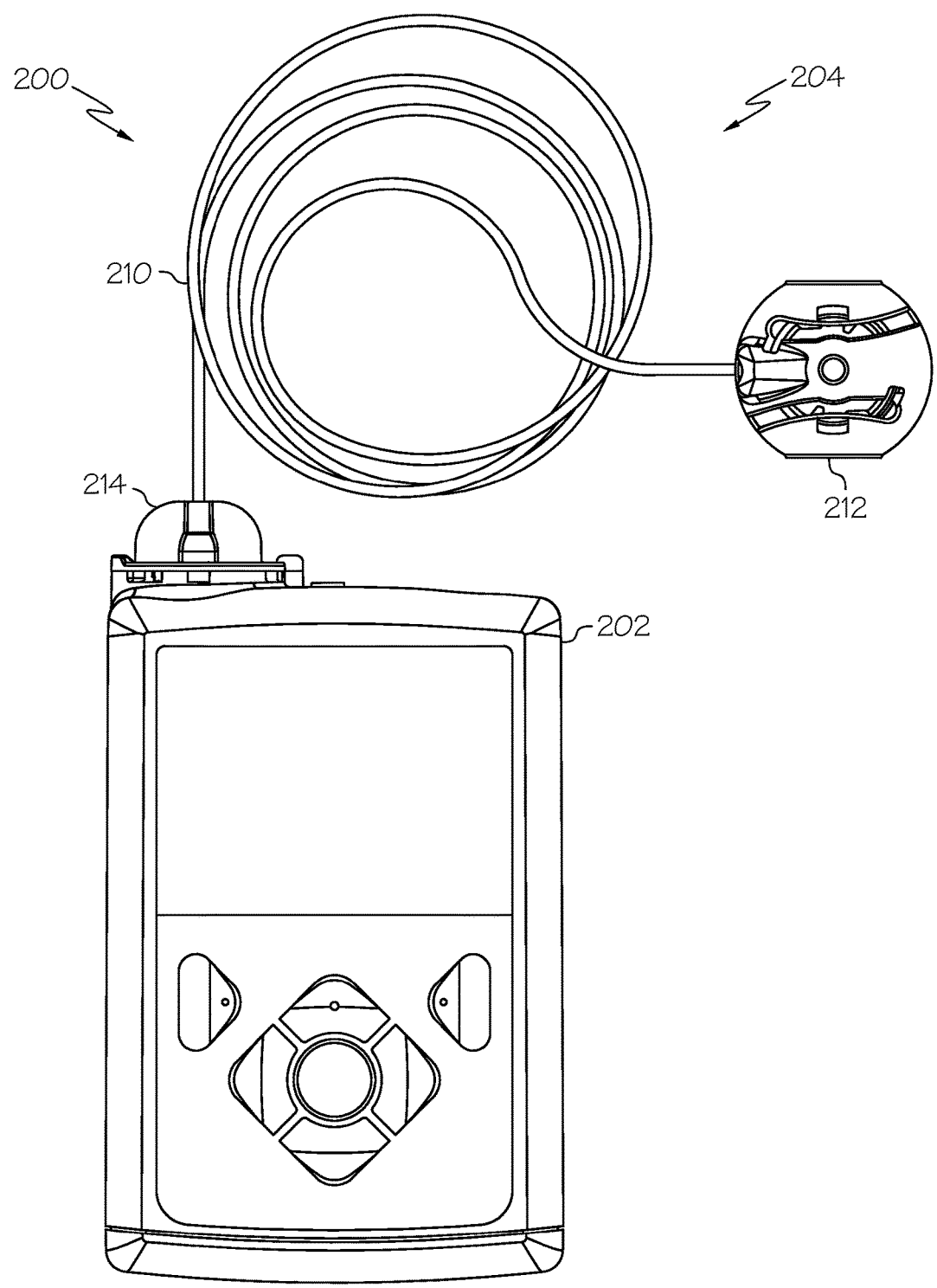
FIG. 2 is a plan view of an exemplary embodiment of a fluid delivery system that includes a fluid infusion device and an infusion set.

The fluid infusion device 102 may be provided in any desired configuration or platform. In accordance with one non-limiting embodiment, the fluid infusion device is realized as a portable unit that can be carried or worn by the patient. In this regard, FIG. 2 is a plan view of an exemplary embodiment of a fluid delivery system 200 that includes a portable fluid infusion device 202 and a fluid conduit assembly that takes the form of an infusion set component 204. For this particular embodiment, the infusion set component 204 can be coupled to the fluid infusion device 202 as depicted in FIG. 2. The fluid infusion device 202 accommodates a fluid reservoir (hidden from view in FIG. 2) for the medication fluid to be delivered to the user.

The illustrated embodiment of the infusion set component 204 includes, without limitation: a tube 210; an infusion unit 212 coupled to the distal end of the tube 210; and a connector assembly 214 coupled to the proximal end of the tube 210. The fluid infusion device 202 is designed to be carried or worn by the patient, and the infusion set component 204 terminates at the infusion unit 212 such that the fluid infusion device 202 can deliver fluid to the body of the patient via the tube 210. The fluid infusion device 202 may leverage a number of conventional features, components, elements, and characteristics of existing fluid infusion devices. For example, the fluid infusion device 202 may incorporate some of the features, components, elements, and/or characteristics described in U.S. Pat. Nos. 6,485,465 and 7,621,893, the relevant content of which is incorporated by reference herein.

The infusion set component 204 defines a fluid flow path that fluidly couples the fluid reservoir to the infusion unit 212. The connector assembly 214 mates with and couples to the neck region of the fluid reservoir, establishing the fluid path from the fluid reservoir to the tube 210. The connector assembly 214 (with the fluid reservoir coupled thereto) is coupled to the housing of the fluid infusion device 202 to seal and secure the fluid reservoir inside the housing. Thereafter, actuation of the fluid infusion device 202 causes the medication fluid to be expelled from the fluid reservoir, through the infusion set component 204, and into the body of the patient via the infusion unit 212 at the distal end of the tube 210. Accordingly, when the connector assembly 214 is installed as depicted in FIG. 2, the tube 210 extends from the fluid infusion device 202 to the infusion unit 212, which in turn provides a fluid pathway to the body of the patient. For the illustrated embodiment, the connector assembly 214 is realized as a removable reservoir cap (or fitting) that is suitably sized and configured to accommodate replacement of fluid reservoirs (which are typically disposable) as needed.

Figure 3:
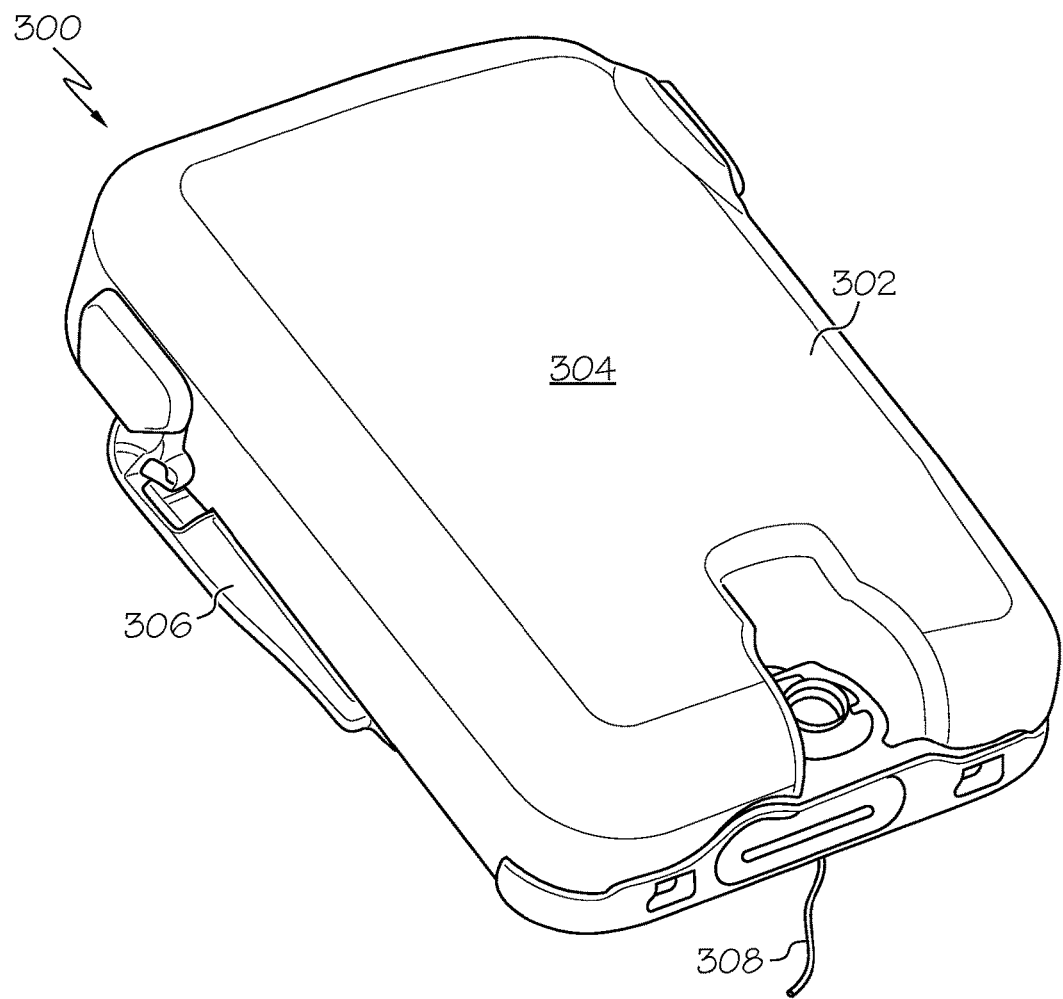
FIG. 3 is a perspective view of an exemplary embodiment of a fluid delivery system that includes a fluid infusion device designed to be affixed to the skin of the user.

FIG. 3 is a perspective view of another exemplary embodiment of a fluid delivery system 300 that includes a fluid infusion device 302 designed to be affixed to the skin of the user. The fluid infusion device 302 includes two primary components that are removably coupled to each other: a durable housing 304; and a base plate 306. The fluid infusion device 302 also includes or cooperates with a removable/replaceable fluid reservoir (which is hidden from view in FIG. 3). For this particular embodiment, the fluid reservoir mates with, and is received by, the durable housing 304. In alternate embodiments, the fluid reservoir mates with, and is received by, the base plate 306.

The base plate 306 is designed to be temporarily adhered to the skin of the patient using, for example, an adhesive layer of material. After the base plate is affixed to the skin of the patient, a suitably configured insertion device or apparatus may be used to insert a fluid delivery needle or cannula 308 into the body of the patient. The cannula 308 functions as one part of the fluid delivery flow path associated with the fluid infusion device 302. In this regard, the cannula 308 may be considered to be one implementation of the fluid conduit assembly 104 shown in FIG. 1 (or a portion thereof).

FIG. 3 depicts the durable housing 304 and the base plate 306 coupled together. For this particular embodiment, the durable housing 304 contains, among other components, a drive motor, a battery, a threaded drive shaft for the fluid reservoir, one or more integrated circuit chips and/or other electronic devices (not shown). The durable housing 304 and the base plate 306 are cooperatively configured to accommodate removable coupling of the durable housing 304 to the base plate 306. The removable nature of the durable housing 304 enables the patient to replace the fluid reservoir as needed.

Figure 4:
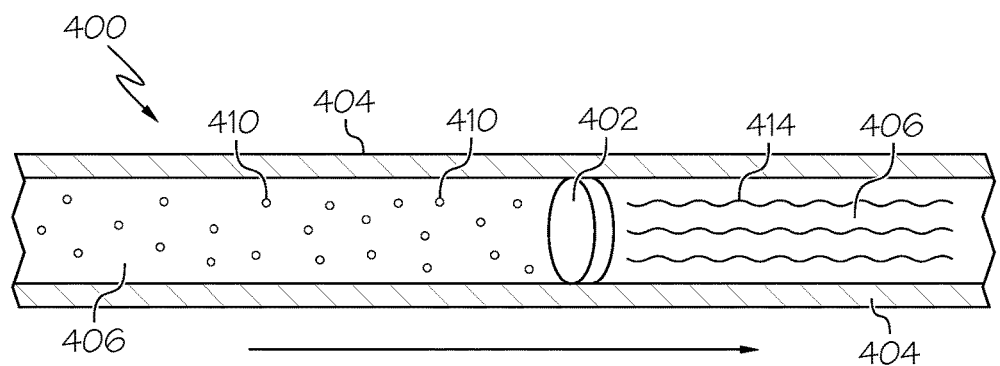
FIG. 4 is a schematic representation of a portion of a fluid conduit assembly.

The fluid delivery systems 200, 300 described here are merely two exemplary embodiments that can include a fluid conduit assembly outfitted with a gas trapping filter. In this regard, FIG. 4 is a schematic representation of a portion of a fluid conduit assembly 400 having a gas trapping filter 402 positioned therein. It should be appreciated that the fluid conduit assembly 400 has been simplified for ease of illustration. In practice, the fluid conduit assembly 400 may be realized in any of the fluid delivery systems described here, and/or in other fluid delivery systems not specifically described in detail here. For example, the fluid conduit assembly 400 may be implemented as, or form a part of, a fluid infusion set, a connector assembly, a fluid reservoir, a fluid reservoir cap, a chamber or internal feature of an infusion pump, or the like.

The fluid conduit assembly 400 is suitably configured to accommodate the delivery of a medication fluid such as insulin. The fluid conduit assembly 400 includes a structure 404 (or structures) defining a flow path 406 for the medication fluid. In FIG. 4, the structure 404 is depicted in cross section, and it resembles a tube. Alternatively, the structure 404 can be a section of a fluid connector (such as a two-part detachable connector), an internal feature of an infusion device, a portion of a fluid reservoir coupler, or the like. In certain embodiments, the structure 404 includes, forms a part of, or is realized as a reservoir cap for a fluid infusion device (see FIG. 6). In some embodiments, the structure 404 includes, forms a part of, or is integrated with an infusion set for a fluid infusion device. In this regard, the gas trapping filter 402 can be integrated with the delivery cannula hub or housing that is located at or near the downstream end of the infusion set. In yet other embodiments, the structure 404 includes, forms a part of, or is realized as a fluid connector, such as a LUER LOK fitting or connector. In certain embodiments, the structure 404 is implemented as a feature of the fluid infusion device. These and other deployments of the fluid conduit assembly 400 are contemplated by this disclosure, and the particular examples presented here are not intended to be limiting or exhaustive.

The flow path 406 is defined by the interior space of the structure 404. The gas trapping filter 402 may be coupled to the structure 404 and positioned in the flow path 406 such that the medication fluid passes through the gas trapping filter 402 during fluid delivery operations. FIG. 4 depicts a straightforward scenario where the gas trapping filter 402 physically obstructs the flow path 406, such that the medication fluid is not diverted around the gas trapping filter 402. In other embodiments, there can be additional fluid flow paths that allow some of the medication fluid to bypass the gas trapping filter 402.

The gas trapping filter 402 is formed from a suitable material, composition, or element such that the medication fluid can easily pass through the gas trapping filter 402 during fluid delivery operations. The gas trapping filter 402 can be formed from a hydrophilic, semi-hydrophilic, partially hydrophilic, or predominantly hydrophilic material. Although a truly hydrophilic material may be ideal, the material used for the gas trapping filter 402 can be partially or predominantly hydrophilic while exhibiting some amount of hydrophobicity. In practice, the gas trapping filter 402 can exhibit up to fifty percent hydrophobicity without adversely impacting the desired performance. For example, the gas trapping filter 402 may include or be fabricated from a hydrophilic membrane, a hydrophilic sponge material, or a hydrophilic foam material. As explained below, the gas trapping filter 402 also serves to filter particulates from the medication fluid during fluid delivery operations. Accordingly, the gas trapping filter 402 has a pore size that is small enough to inhibit the flow of particulates. In certain embodiments, the pore size is within the range of about 0.45 to 5.00 microns, which is suitable for most medical applications. Non-limiting examples of suitable materials for the gas trapping filter 402 include: polyacrylate; polyurethane; nylon; cellulose acetate; polyvinyl alcohol; polyethelene foam; polyvinyl acetate; polyester fiber felt; polyester (PET); polysulfone; polyethyl sulfone; collagen; polycaprolactone; or the like. It should be appreciated that the material or materials used to fabricate the gas trapping filter 402 can be treated to enhance the hydrophilic characteristics if so desired.

One function of the gas trapping filter 402 is to inhibit the downstream flow of air bubbles. Depending on the particular composition and configuration of the gas trapping filter 402, air bubbles 410 (depicted as small circles in the flow path 406 upstream of the gas trapping filter 402) can be blocked by the gas trapping filter 402 and/or retained within the gas trapping filter 402 as the liquid medication flows downstream. Thus, the gas trapping filter 402 may be realized as a gas impermeable membrane or material that also exhibits good hydrophilic properties. In some embodiments, the gas trapping filter 402 can be fabricated from material having micro-cavities formed therein for trapping and retaining gas bubbles from the medication fluid. FIG. 4 illustrates a scenario where the air bubbles 410 are removed from the medication fluid. Accordingly, no air bubbles 410 are present in the medication fluid that resides downstream from the gas trapping filter 402.

Another benefit of the gas trapping filter 402 relates to the volume accuracy of the fluid delivery system. In certain implementations, syringe pumps are calibrated to deliver a specified volume in response to a controlled mechanical actuation (e.g., movement of the syringe plunger in response to controlled rotation of an electric motor). Reducing or eliminating air from the fluid delivery path increases the accuracy of the volume calibrations.

In certain embodiments, the gas trapping filter 402 also serves to filter particulates from the medication fluid such that the particulate count of the downstream medication fluid is reduced. As mentioned above, the material used to fabricate the gas trapping filter 402 can be selected with a desired pore size to accommodate filtering of particulates having an expected size.

In some embodiments, the gas trapping filter 402 also serves to absorb and/or adsorb certain substances, chemicals, or suspended elements from the medication fluid. For example, the gas trapping filter 402 may include material that is configured or treated to absorb/adsorb lubricating or manufacturing oil that is associated with the manufacturing, assembly, or maintenance of one or more components of the fluid delivery system. In this regard, a fluid reservoir for insulin can be fabricated with a trace amount of silicone oil that serves as a lubricant for the plunger of the reservoir. Accordingly, the gas trapping filter 402 can include a material, layer, or treatment that reduces, traps, or otherwise removes some or all of the silicone oil from the medication fluid as it passes through the gas trapping filter 402.

In particular embodiments, the gas trapping filter 402 also serves as a drug depot during operation of the fluid delivery system. To this end, the gas trapping filter 402 can include a drug, medicine, chemical, or composition impregnated therein (or coated thereon, or otherwise carried by the gas trapping filter 402). A quantity of the drug is released into the medication fluid as the fluid flows through the gas trapping filter 402 during a fluid delivery operation. The wavy lines 414 in FIG. 4 schematically depict the drug after it has been released into the downstream medication fluid. In practice, the drug carried by the gas trapping filter 402 will eventually be depleted unless the gas trapping filter 402 or the fluid conduit assembly 400 is replaced before depletion. The drug carried by the gas trapping filter 402 can be selected to address the needs of the particular patient, fluid delivery system, medication fluid, etc. In accordance with the exemplary insulin infusion system described here, the gas trapping filter 402 is impregnated with a drug that treats the patient site to extend the useful life of the fluid infusion set. For example, the gas trapping filter 402 can be treated with an anticoagulant such as Heparin or Dextran. As another example, the gas trapping filter 402 can be impregnated or infused with an anti-proliferative drug such as Rapamycin. It should be appreciated that these examples are neither exhaustive nor restrictive, and that the gas trapping filter 402 can be impregnated, treated, or infused with any drug that may be appropriate and suitable for the particular medical condition, fluid delivery system, or application.

Although FIG. 4 shows a single component that serves as the gas trapping filter 402, an embodiment of the fluid conduit assembly 400 can utilize a plurality of physically distinct elements that collectively function as the gas trapping filter 402. For example, the gas trapping filter 402 can be fabricated from different materials that are selected for their properties and characteristics (gas trapping, oil absorption, oil adsorption, particulate filtering). Moreover, certain embodiments of the fluid delivery system can be outfitted with multiple gas trapping filters located in different sections of the fluid flow path. For example, one filter component can be positioned at or near the fluid reservoir, and another filter component can be positioned at or near the distal end of the fluid infusion set. These and other practical implementations are contemplated by this disclosure.

Figure 5:
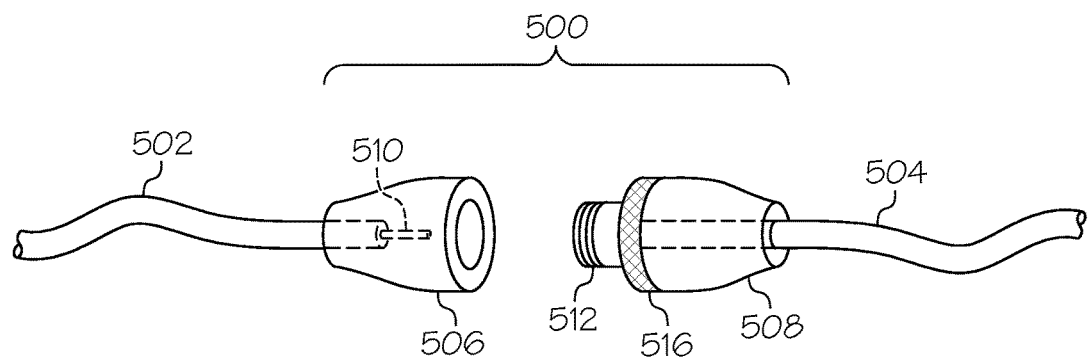
FIG. 5 is an exploded and partially phantom view of a connector assembly suitable for use with a fluid conduit.

As mentioned above, the fluid conduit assembly that carries the gas trapping filter can be realized in a number of different forms. For example, the fluid conduit assembly may include or be realized as a fluid connector, where the gas trapping filter is integrated in the fluid connector. In this regard, FIG. 5 is an exploded and partially phantom view of a fluid connector assembly 500 suitable for use with a fluid conduit assembly. The illustrated embodiment of the fluid connector assembly 500 functions to physically and fluidly couple an upstream section of tubing 502 to a downstream section of tubing 504. The fluid connector assembly 500 includes a first connector 506 (which is physically and fluidly coupled to the upstream section of tubing 502) that mates with a second connector 508 (which is physically and fluidly coupled to the downstream section of tubing 504). The first connector 506 includes a hollow needle 510 that provides a fluid flow path from the upstream section of tubing 502. The second connector 508 includes a septum 512 that receives the hollow needle 510 when the first connector 506 engages the second connector 508. When the two connectors 506, 508 are engaged and locked together, the medication fluid can flow from the upstream section of tubing 502, through the hollow needle 510, and into the downstream section of tubing 504.

One or both of the connectors 506, 508 can be provided with a gas trapping filter having the characteristics and functionality described previously. For this particular embodiment, a unitary gas trapping filter 516 is integrated in the second connector 508. The gas trapping filter 516 is located within the body of the second connector 508, and it resides downstream from the septum 512. During a fluid delivery operation, the medication fluid exits the hollow needle 510, enters the second connector 508 (e.g., into a space that is upstream from the gas trapping filter 516), and is forced through the gas trapping filter 516 before it passes into the downstream section of tubing 504.

Figure 6:
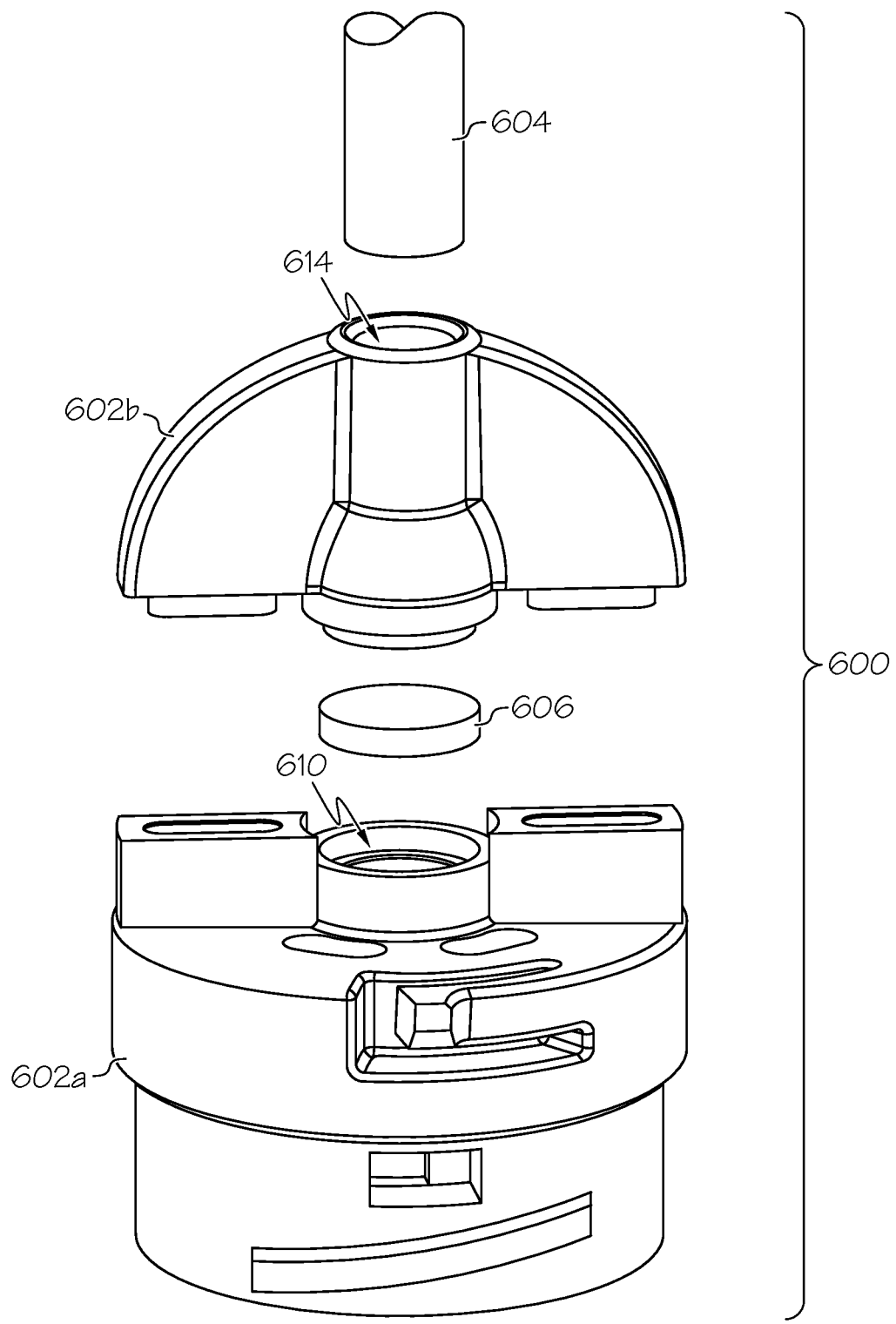
FIG. 6 is an exploded perspective view of an embodiment of a fluid conduit assembly that is realized as a cap for a fluid reservoir.

As another example, a fluid conduit assembly configured as described herein may include or be realized as an infusion set for a fluid infusion pump, where the gas trapping filter is integrated in the infusion set. In this regard, FIG. 6 is an exploded perspective view of a fluid conduit assembly that is realized as a cap or a connector assembly 600 for a fluid reservoir. In this regard, the connector assembly 600 is generally configured as described above for the connector assembly 214 shown in FIG. 2. Accordingly, the connector assembly 600 may be provided as component of a disposable infusion set.

The illustrated embodiment of the connector assembly 600 generally includes, without limitation: a body section 602; a flow path defined in the body section 602; a length of tubing 604 extending from the body section 602; and a gas trapping filter 606. FIG. 6 depicts the body section 602 separated into two constituent parts: a lower body section 602a; and an upper body section 602b. The lower body section 602a can be affixed to the upper body section 602b (for example, by sonic welding or using an adhesive) after installing the gas trapping filter 606 into a retaining cavity 610 formed within the lower body section 602a. In alternative embodiments, the body section 602 can be fabricated as a one-piece component by molding a suitable material while encapsulating the gas trapping filter 606 inside the body section 602.

The lower body section 602b is suitably configured to receive a fluid reservoir, e.g., by a threaded engagement, a snap fit, tabs, or the like. The tubing 604 is physically and fluidly coupled to the upper body section 602b such that the tubing 604 is in fluid communication with the flow path. This allows the tubing 604 to carry fluid from the body section 602 during a fluid delivery operation. The flow path, much of which is hidden from view in FIG. 6, may be defined by: a hollow needle that penetrates a septum of the fluid reservoir; an internal space, chamber, or conduit of the lower body section 602a, which is upstream of the gas trapping filter 606; and an internal space, chamber, or conduit 614 of the upper body section 602b, which is downstream of the gas trapping filter 606. The flow path continues into the tubing 604, which is connected to the upper body section 602b.

The gas trapping filter 606 is secured within the body section 602 such that it is positioned in the flow path of the medication fluid. During a fluid delivery operation, the medication fluid is forced out of the fluid reservoir and into the hollow needle (not shown in FIG. 6). The distal end of the hollow needle terminates at a location that is upstream of the gas trapping filter 606. This positioning ensures that the medication fluid can be filtered and otherwise treated by the gas trapping filter 606 before it exits the connector assembly 600. As explained above, the gas trapping filter 606 is suitably configured to reduce the amount of air bubbles in the downstream medication fluid, and to reduce the amount of particulates in the downstream medication fluid.

Figure 7:
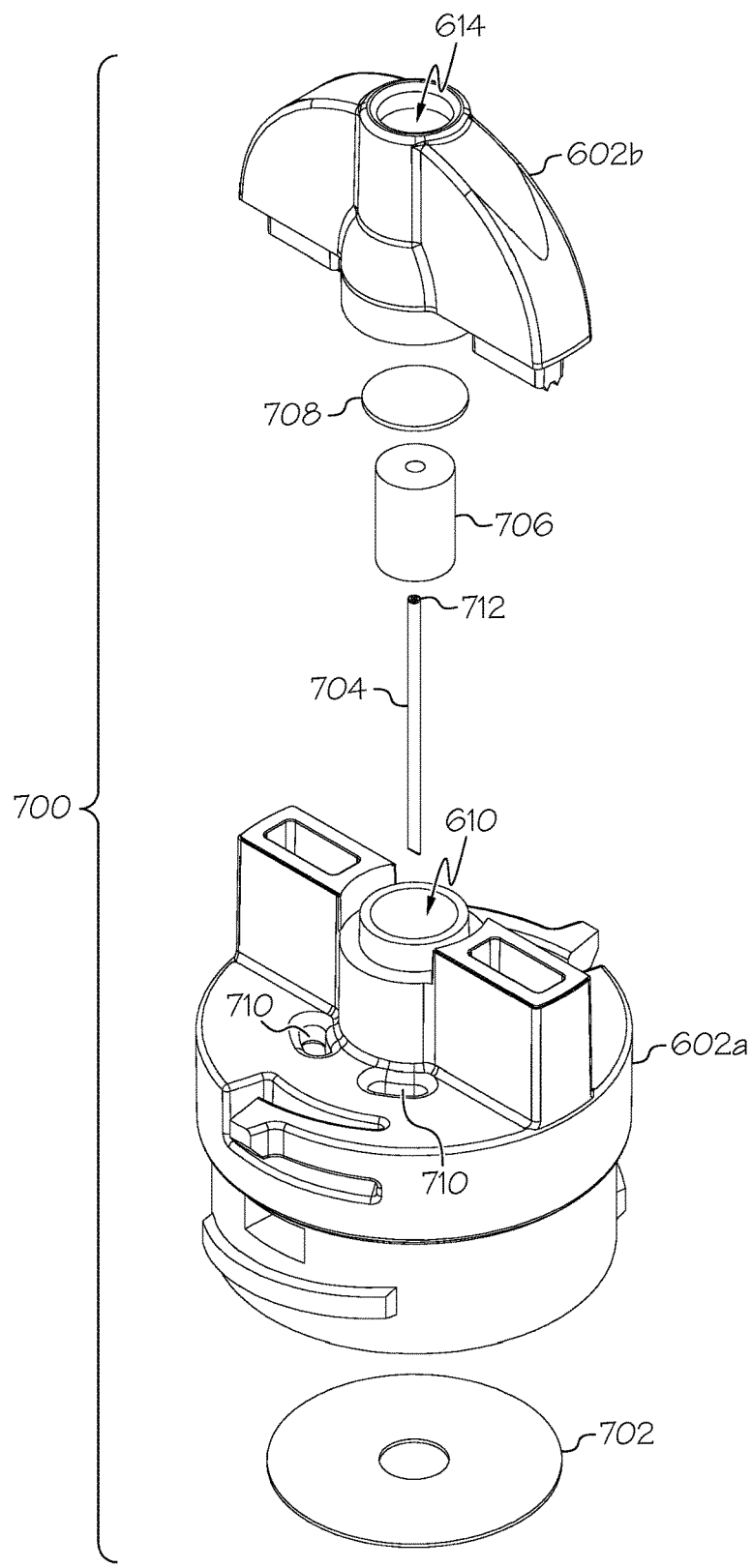
FIG. 7 is an exploded perspective view of another embodiment of a fluid conduit assembly that is realized as a cap for a fluid reservoir.

FIG. 7 is an exploded perspective view of another embodiment of a fluid conduit assembly 700 that is realized as a cap for a fluid reservoir. The assembly 700 shares some elements and features with the assembly 600 and, therefore, common elements and features will not be redundantly described here in the context of the assembly 700. As mentioned previously, the connector assembly 700 may be provided as component of a disposable infusion set.

The illustrated embodiment of the connector assembly 700 generally includes, without limitation: a body section 602 (having a lower body section 602a and an upper body section 602b); a venting membrane 702; a hollow needle 704; a gas trapping filter 706; and a reservoir membrane 708. These components can be assembled together in the manner generally described above for the assembly 600.

The venting membrane 702 can be affixed to the upper interior surface of the lower body section 602a such that the venting membrane 702 covers one or more vent holes 710 formed in the top portion of the lower body section 602a. The vent holes 710 facilitate venting of the reservoir chamber that resides in the housing of the fluid infusion device (see, for example, FIG. 2). The hollow needle 704 can be affixed to the lower body section 602a such that the downstream end 712 of the hollow needle 704 resides below or within the gas trapping filter 706 after the fluid conduit assembly 700 is fabricated. The positioning of the downstream end 712 is important to ensure that the medication fluid is forced through the gas trapping filter 706 during fluid delivery operations. The reservoir membrane 708 can be affixed within a cavity formed in the upper body section 602b (the cavity is hidden from view in FIG. 7). The reservoir membrane 708 is at least partially hydrophilic to allow the medication fluid to pass during fluid delivery operations.

The gas trapping filter 706 is secured within the body section 602 such that it is positioned in the flow path of the medication fluid. For the illustrated embodiment, the gas trapping filter 706 may be positioned between the reservoir membrane 708 and the downstream end 712 of the hollow needle 704. In certain embodiments, the gas trapping filter 706 is realized as a foam, sponge, or felt fiber composite material. Although not always required, the material used for the gas trapping filter 706 may include, without limitation: polyvinyl acetate (PVA); polyvinyl alcohol; polyester (PET); polycarbonate; polyurethane; polyethyl sulfone; collagen; polycaprolactone; or any combination thereof. In accordance with certain embodiments, a felt-based gas trapping filter 706 has a pore size within the range of about one to 100 microns, and preferably within the range of about 20 to 40 microns. In accordance with certain embodiments, a sponge-based gas trapping filter 706 has a pore size within the range of about 20 to 1000 microns. Regardless of its composition and configuration, the gas trapping filter 706 is suitably configured to reduce the amount of air bubbles in the downstream medication fluid, and to reduce the amount of particulates in the downstream medication fluid.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid delivery system comprising:
a fluid infusion pump to deliver a medication fluid from a fluid reservoir, the fluid infusion pump comprising a housing and a reservoir chamber that resides in the housing, the reservoir chamber accommodating the fluid reservoir; and
a reservoir cap for the fluid reservoir, coupled to the fluid infusion pump to deliver the medication fluid to a user, the reservoir cap defining a flow path for the medication fluid;
the reservoir cap comprising:
a lower body section that engages the fluid reservoir, the lower body section comprising a retaining cavity formed therein, and further comprising a plurality of vent holes formed in a top portion of the lower body section, the lower body section configured to couple with the housing of the fluid infusion pump, and configured to seal and secure the fluid reservoir inside the reservoir chamber, and the plurality of vent holes facilitating venting of the reservoir chamber;
a venting membrane affixed to an upper interior surface of the lower body section and covering the plurality of vent holes;
a hollow needle in the lower body section, the hollow needle fluidly coupling the fluid reservoir to the retaining cavity when the lower body section is coupled to the fluid reservoir;
an upper body section affixed to the lower body section, the upper body section comprising a conduit coupled to a length of tubing extending from the upper body section and in fluid communication with the hollow needle, the length of tubing carrying medication fluid from the upper body section during a fluid delivery operation;
a gas trapping filter positioned in the flow path to filter particulates from the medication fluid, and the gas trapping filter having micro-cavities formed therein to retain and trap gas bubbles from the medication fluid; and
a hydrophilic reservoir membrane affixed within a cavity formed in the upper body section, to allow the medication fluid to pass during the fluid delivery operation, wherein the gas trapping filter is positioned between the reservoir membrane and a downstream end of the hollow needle;
wherein the gas trapping filter is positioned in the retaining cavity downstream of the hollow needle, upstream of the conduit, and upstream of the length of tubing;
wherein the gas trapping filter physically obstructs a fluid flow path into the length of tubing such that the medication fluid is not diverted around the gas trapping filter, and to inhibit downstream flow of gas bubbles into the length of tubing; and
wherein the fluid flow path is defined by the hollow needle, the retaining cavity of the lower body section, the conduit of the upper body section, and the length of tubing, such that during the fluid delivery operation the medication fluid is forced out of the fluid reservoir, into the hollow needle, into the retaining cavity of the lower body section, through the gas trapping filter, into the conduit of the upper body section, and through the length of tubing.

2. The fluid delivery system of claim 1, wherein:
the gas trapping filter comprises a drug impregnated therein; and
a quantity of the drug is released into the medication fluid as the medication fluid flows through the gas trapping filter during a fluid delivery operation.

3. The fluid delivery system of claim 1, wherein the gas trapping filter has a pore size within the range of 0.45 to 5.00 microns.

4. A reservoir cap for a reservoir of a medication fluid, the reservoir cap comprising:
- a lower body section to receive the reservoir of medication fluid, the lower body section comprising a retaining cavity formed therein, and further comprising a plurality of vent holes formed in a top portion of the lower body section, the lower body section configured to couple with a housing of a fluid infusion device that controls delivery of the medication fluid from the reservoir, and configured to seal and secure the fluid reservoir inside a reservoir chamber that resides in the housing, and the plurality of vent holes facilitating venting of the reservoir chamber;
- a venting membrane affixed to an upper interior surface of the lower body section and covering the plurality of vent holes;
- a hollow needle in the lower body section, the hollow needle carrying fluid from the reservoir of medication fluid into the retaining cavity when the lower body section is coupled to the reservoir of medication fluid;
- an upper body section affixed to the lower body section, the upper body section comprising a conduit coupled to a length of tubing extending from the upper body section and in fluid communication with the hollow needle, the length of tubing carrying medication fluid from the upper body section during a fluid delivery operation;
- a partially hydrophilic gas trapping filter positioned in the retaining cavity downstream of the hollow needle, upstream of the conduit, and upstream of the length of tubing to filter particulates from the medication fluid, the gas trapping filter having micro-cavities formed therein to retain and trap gas bubbles from the medication fluid; and
- a hydrophilic reservoir membrane affixed within a cavity formed in the upper body section, to allow the medication fluid to pass during the fluid delivery operation, wherein the gas trapping filter is positioned between the reservoir membrane and a downstream end of the hollow needle;
- wherein the gas trapping filter physically obstructs a fluid flow path into the length of tubing such that the medication fluid is not diverted around the gas trapping filter, and to inhibit downstream flow of gas bubbles into the length of tubing; and
- wherein the fluid flow path is defined by the hollow needle, the retaining cavity of the lower body section, the conduit of the upper body section, and the length of tubing, such that during the fluid delivery operation the medication fluid is forced out of the fluid reservoir, into the hollow needle, into the retaining cavity of the lower body section, through the gas trapping filter, into the conduit of the upper body section, and through the length of tubing.

5. The reservoir cap of claim 4, wherein:
- the gas trapping filter comprises a drug impregnated therein; and
- a quantity of the drug is released into the medication fluid as the medication fluid flows through the gas trapping filter.

6. The reservoir cap of claim 4, wherein the gas trapping filter has a pore size within the range of 0.45 to 5.00 microns.

7. The reservoir cap of claim 4, wherein the gas trapping filter adsorbs or absorbs lubricating oil associated with manufacturing of the reservoir.

8. The reservoir cap of claim 4, wherein the gas trapping filter comprises a partially hydrophilic membrane.

9. The reservoir cap of claim 4, wherein the gas trapping filter comprises a partially hydrophilic sponge, felt, or fiber composite material.

10. The reservoir cap of claim 4, wherein the gas trapping filter adsorbs or absorbs silicone oil.

\* \* \* \* \*